(12) United States Patent
Hutchings et al.

(10) Patent No.: US 7,651,763 B2
(45) Date of Patent: *Jan. 26, 2010

(54) SUSTAINED RELEASE AIR FRESHENING DEVICE

(75) Inventors: David Allen Hutchings, Dublin, OH (US); Robert Bernard Fechter, Worthington, OH (US); Edward Gerard Toplikar, Hilliard, OH (US); Raymond Scott Harvey, Worthington, OH (US); Robert Andrew Cassidy, Columbus, OH (US); Frances Ellen Lockwood, Georgetown, KY (US); Wen-Chen Su, Lexington, KY (US)

(73) Assignee: Ashland Licensing and Intellectual Property, LLC, Dublin, OH (US)

( * ) Notice: Subject to any disclaimer, the term of this patent is extended or adjusted under 35 U.S.C. 154(b) by 350 days.

This patent is subject to a terminal disclaimer.

(21) Appl. No.: 10/967,448

(22) Filed: Oct. 18, 2004

(65) Prior Publication Data

US 2006/0083709 A1   Apr. 20, 2006

(51) Int. Cl.
| | |
|---|---|
| *B23B 5/14* | (2006.01) |
| *C07F 9/02* | (2006.01) |
| *C07C 381/00* | (2006.01) |
| *B41J 2/01* | (2006.01) |
| *A61L 9/04* | (2006.01) |
| *C08G 18/67* | (2006.01) |

(52) U.S. Cl. .............. 428/308.4; 428/41.5; 508/325; 522/174; 523/102; 347/1

(58) Field of Classification Search ............. None
See application file for complete search history.

(56) References Cited

U.S. PATENT DOCUMENTS

2005/0215725 A1 *   9/2005   St. Clair ................. 525/314

* cited by examiner

*Primary Examiner*—Shanon A Foley

(74) *Attorney, Agent, or Firm*—Wood, Herron & Evans, LLP

(57) ABSTRACT

This invention relates to a device that provides controlled release of a fragrant or deodorizing substance: the fragrant or deodorizing substance being solubilized with an appropriate carrier solvent within a polymeric matrix. The layers function as protective barriers, semi-permeable membranes, fragrance reservoirs, and adhesives. The device is capable of delivering a fragrance at a controlled rate for a prolonged period of time through the gradual diffusion and release of fragrant material carried by a solvent from a reservoir system to the semi-permeable UV curable, oligomer composition acting a fragrance release regulator. Additionally, the UV curable, oligomeric composition that forms the reservoir and regulating layer can be engineered to be adhesive through cure inhibition. The method of cure inhibition can also be utilized to create internal areas of high and low cross link density to further control the release rate of a fragrance.

13 Claims, 7 Drawing Sheets

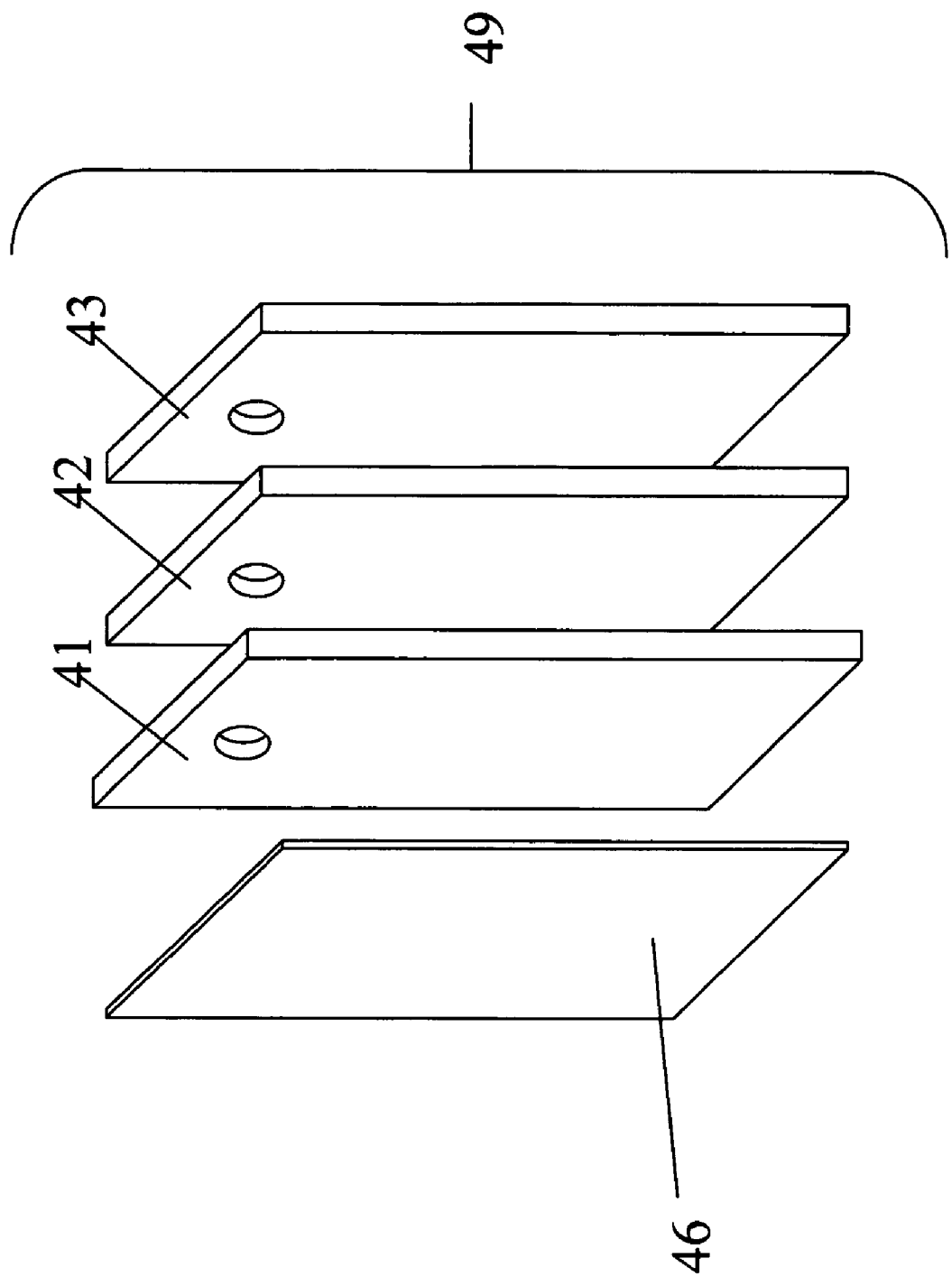

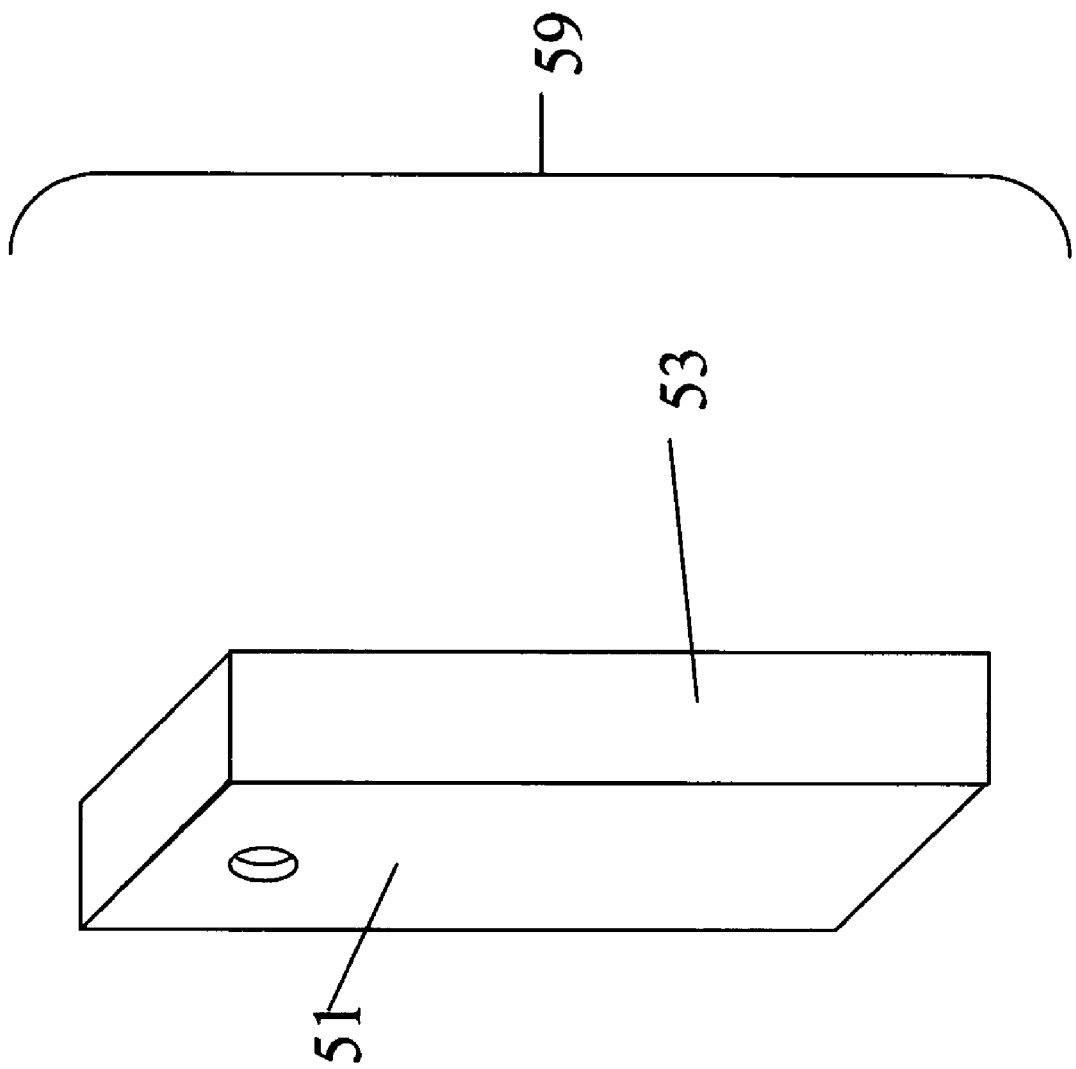

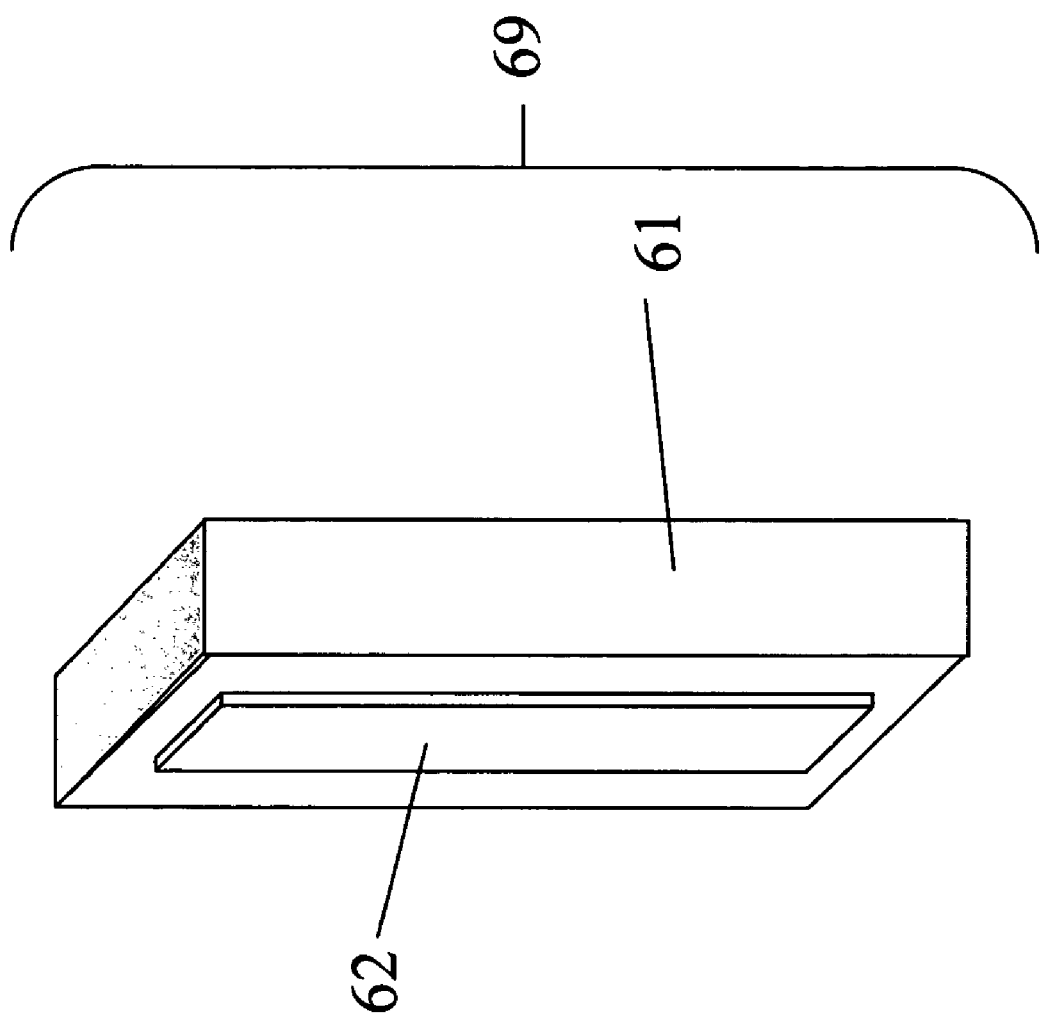

SUSTAINED RELEASE AIR FRESHENING DEVICE

BACKGROUND OF THE INVENTION

1. Field of the Invention

This invention relates to a device that provides controlled release of a fragrant or deodorizing substance: the fragrant or deodorizing substance being solubilized in a carrier solvent within a polymeric matrix. The device can be mounted in almost any location but it is primarily intended for use inside an automobile by hanging from a rearview mirror or adhering to a window or another substantially flat surface. The device can be transparent so as to be inconspicuous or to permit viewing of an image bearing layer or may be colored by methods known to those skilled in the art.

2. Problems in the Art

Modification of the odor of the surrounding air has long been accomplished through the use of fragrant materials or deodorizing agents to mask and even neutralize offending odors. Malodor has been shown to cause nausea, headaches, coughing, irritation of mucous membranes, and shortness of breath. The need for odor modification is greatest in locations with an increased likelihood of offending odors, such as restrooms and kitchens, and in confined locations where people spend a considerable amount of time, such as an office or in an automobile.

Numerous methods to combat malodor in automobiles are documented in the patent literature. U.S. Pat. No. 4,814,212, Automobile Air Freshener Unit, by Spector (Mar. 21, 1989), describes adhesively attaching a framed replaceable gel air freshener to a car window. However, the Spector invention fails to provide any control over the rate of release and the device not a multi-laminate multi-layer device which possesses the advantages of such a system. Similar devices may be hung from rear view mirrors and can employ paper or cardboard substrates as fragrance reservoirs. Product use recommendations for such air fresheners provide an impractical procedure involving the gradual removal of the protective barrier film in order to manually regulate the rate of fragrance release over the period of use.

Air fresheners that attach to or are inserted into air filters are described in U.S. Pat. No. 3,577,710, Air-Treatment Apparatus, by Feldman (May 4, 1971); U.S. Pat. No. 3,902,877, Container for Air Treating Agent, by Swaim (Jun. 7, 1977); U.S. Pat. No. 4,563,333, Deodorizing Fitting for Air Filters, by Ward (Jan. 5, 1986); and Japanese Patent JPO 04151438, Method and Apparatus for Generating Perfume, by Toshio (May 25, 1992). None of the aforementioned inventions are intended for use in the passenger compartment of an automobile.

Air fresheners that are intended for use in the passenger compartment of an automobile and attachable to the air vents are described in U.S. Pat. No. 5,269,723, Vehicle Air Freshener, by Bender (Dec. 14, 1993); U.S. Pat. No. 5,865,372, Air Freshener for Vehicle, by Ceresko (Feb. 2, 1999); U.S. Pat. No. 6,103,201, Propellar Air Freshener, by Green (Aug. 15, 2000); U.S. Pat. No. 6,123,906, Air Freshening Device for Automobiles, by Blount (Mar. 6, 2001); and U.S. Pat. No. 6,416,043, Louver Air Freshener, by Eisenbaum (Jul. 9, 2002). While the aforementioned devices are suitable for use in an automobile, they do not have a rate controlling mechanism and are only mountable on the vent louvers of the automobile air system.

Air fresheners that are intended for use in the passenger compartment of an automobile, possessing a features to provide limited control over the rate of release of the fragrance, are described in U.S. Pat. No. 4,686,353, Aroma-Generating Automobile Cigarette Lighter, by Spector (Aug. 11, 1987); U.S. Pat. No. 5,373,581, Automobile Plug-In Air Freshener With Rotatable Switch And Vaporizer, by Smith (Dec. 13, 1994); U.S. Pat. No. 5,394,506, Fragrance Dispenser For An Automobile, by Stein (Feb. 28, 1995); U.S. Pat. No. 5,788,931, Air Freshener For Motor Vehicles, by Quintana (Aug. 4, 1998); U.S. Pat. No. 6,021,254, Timed Electric Vehicular Air Freshener, by Hunter (Feb. 1, 2000); and U.S. Patent Application 2002/0176704, Air Freshener For Motor Vehicles, by Roe (Nov. 28, 2002). All of the aforementioned inventions utilize automobile DC socket cigarette lighter to heat a substrate and release a fragrance. U.S. Pat. No. 6,021,254 adds a timer that allows the invention to release fragrance at timed intervals. U.S. Patent Application 2002/176704 allows the user to modify the rate of release by varying the current supplied to a light bulb acting as the heating element for the device. All of the above inventions require active rate control measures on behalf of the user and still provide insufficient control over the release of a fragrance to avoid a fragrance spike early in the life cycle of the fragrance containing substrate. Additionally, the all of the devices occupy a DC socket, a useful automobile appliance, and detract from the aesthetics of the automobile interior.

These prior methods, while useful, fall short of meeting consumer expectations. The most significant problem is the inability of prior devices to regulate the release of the fragrance to achieve a constant release rate. While there have been devices which have made gains in this area through the use of reservoirs surrounded by a rate controlling membrane, none have been entirely successful. Additionally, the duration of such devices is extremely limited, requiring frequent replacement. U.S. Pat. No. 4,874,129 by DiSapio et al. utilizes a multi-layer multi-laminate silicone based device to achieve it's goal of regulating the release of the fragrance. The '129 patent, unlike the present invention, requires layers comprised of adhesives to bind additional layers to the reservoir, uses silicone based oligomers, does not use an additional layer similar to the reservoir to diffuse the fragrance/solvent mix into before release and does not mention doping such a layer to facilitate diffusion, does not modify the cross-link density in order to modify the release rate, and the photo-cure polymer cannot be cured to produce an adhesive cure at desired areas on the surface.

In the published unexamined Japanese Patent Application No. 2000086781 by Takashi et al., the patentee describes photopolymerizing a resin of urethane acrylate oligomer, single organic-function (meta) acrylate, polyfunctional (meta) acrylate, a perfume component, and a photopolymerization initiator to achieve a film which stores perfume. However, the invention described in the Takashi application utilizes urethane acrylates modified to create flexible linkages and blended with other monomers. The present invention does not require modified urethane acrylates and is not blended with other monomers. The present invention utilizes a polybutadiene backbone not described in the Takashi application.

The Takashi device also requires low cross-link densities and low viscosities in order to apply the resin as a coating on sheets while the UV curable, oligomeric composition of the present invention has a significantly higher viscosity. The significantly higher viscosity and cross-link density of the present invention also produces a device which resists shrinkage and cracking thus increasing the useful life of the product by delaying the degradation of the device.

SUMMARY OF THE INVENTION

The invention is directed to the use of an improved means for distributing a fragrance by employing an oligomeric system made by the Michael addition of β-dicarbonyl donor compounds with mixtures of hydroxyl-functional acrylates and multifunctional acrylates receptor compounds to store and release a fragrant material in a controlled fashion over an extended period of time. The novel UV curable, liquid oligomeric composition (derived from the reaction of the Michael addition product and the isocyanate capped polybutadiene) incorporates a butadiene backbone in the UV curable, oligomeric composition. The UV curable, oligomeric composition can be cured in the presence of a fragrance and optional carrier solvent for the fragrance. It is the cured residue of the UV curable, oligomeric composition that is utilized in various applications as a controlled release air freshener.

The presence of the isocyanate capped polybutadiene makes the UV curable, liquid oligomeric composition more accepting of fragrance based materials and helps to overcome the deficiencies in typical UV curable materials. These deficiencies are typically observed as shrinkage, brittleness, and cracking. The presence of the polybutadiene helps to greatly enhance the flexibility of the system allowing for thick films, e.g. about 60 mil, of fragrance containing UV curable, oligomeric composition to be cast and cured. These materials are more amenable to loss of the fragrance while still exhibiting plasticity. In addition, shrinkage of the system and the corresponding cracking that is present in typical UV curable materials is significantly reduced or in many cases eliminated.

The UV curable, oligomeric composition produces unique gel systems when radiation cured in combination with fragrances. Said fragrance gels have been shown to hold fragrance molecules and their excipient or carrier solvents at high levels, i.e. up to 60% by mass and preferably from 30% to 50% by mass, and to release said fragrances in a regulated or controlled fashion over several weeks. These materials are capable of forming fragrance containing films, but show substantial shrinkage during the fragrance release cycle in comparison with fragrance containing films prepared using the UV curable, liquid oligomer systems taught in this invention. The UV curable, liquid oligomeric composition of the present invention can be selectively cured to produce adhesive surface areas by either modulating the radiation or inhibiting the cure. Cure inhibition can be achieved within the UV curable, oligomeric composition through selectively choosing a fragrance that will inhibit the cure thus create pockets of low and high cross-link density.

On cure, the fragrance, excipient, matrix gel system contains swelled polybutadiene domains carrying the incorporated fragrance and it's solvent. In the subject system, the most effective solvents are those which have a high polarity as well as hydrophobiscity. An example of this would be the hexane glycols. While not wishing to be bound by theory it is believed that the systems readily compatibilize with the polybutadiene segments through their aliphatic constituents, while their hydroxyl constituents bond with the polar fragrance molecules. Diffusion of the solvent to the gel surface also results in a migration of the fragrance to the surface since it is dragged along through the polar interactions. Evaporation of solvent at the gel surface decreases surface polarity and increases the ease of fragrance molecule volatilization.

The invention is preferably a multi-layered multi-laminate which uses the preferred gel or UV cured, oligomeric composition as a reservoir impregnated with a fragrant oil and a suitable carrier solvent to aid diffusion. Diffusion to the surface of the gel is controlled by areas of high and low cross-link density that impede the movement of the solvent and subsequent transport of the fragrant oil. The ability to create a selectively adhesive gel allows the potential elimination of adhesives to bond additional layers directly to the gel. This additional layer acts to further control diffusion and thus regulate the release of the fragrance to achieve a release of fragrance which is both prolonged and consistent over time. This additional layer acts to further control diffusion and thus regulate the release of the fragrance to achieve a release which is both prolonged and consistent over time. If an adhesive were required, this could prevent the use of a second gel layer as a regulator. Similar systems using appropriate adhesives with or without channels to permit solvent migration are anticipated by this invention.

One advantage of the present invention is that it can be clear and transparent. Other commercially available fragrance storing compositions are typically opaque. Those commercially available fragrance storing compositions that tend to be somewhat transparent tend to have a yellow tint. Image bearing layers can be included in the device to display logos, messages, pictures, or aesthetically pleasing designs. Additionally, layers which can receive ink from a printer may also be affixed, thus allowing the consumer to personalize their own air freshener. The device may be selectively cut and shaped into aesthetically pleasing two or three dimensional forms. The present invention also minimizes shrinkage, thus inhibiting the cracking and splitting seen in other gel air fresheners due to the relatively high viscosity of the UV curable, oligomeric composition and its higher cross-link density.

The device may be mounted several different ways depending upon the environment and preference of the user. In one embodiment it may be hung from a mirror with either a gel reservoir or a paper blotter reservoir. In another embodiment the device is mounted to a window using a layer that can cling to the window using static cling. In yet another embodiment the device is adhesively attached to the window or another sufficiently flat surface within an automobile.

The duration of fragrance release from the device is dependant upon the choice of fragrance and carrier solvent combinations. Sustained release of a consistent amount of fragrance has been noted from between 30 to 45 days for various systems. As the technology is further developed it is anticipated that these release times will be extended. The regulation of the release of the fragrance also allows the device to minimize or potentially eliminate the fragrance "spike" present in other inventions, whereby the rate of release is initially very high and is dramatically reduced over time. This reduction in fragrance release requires frequent changing of air fresheners in order to keep a sufficient amount of fragrance available for odor masking or deodorizing.

BRIEF DESCRIPTION OF THE DRAWINGS

FIG. 1-5 are exploded perspective views of multi-layered embodiments of the device.

FIG. 6 depicts a multi-layered or single layer encased with a protective cover so as to only expose one surface.

FIG. 7 is a cross-sectional perspective view of a reservoir encased within the UV cured, liquid oligomer.

DETAILED DESCRIPTION OF THE INVENTION

Figure 1:
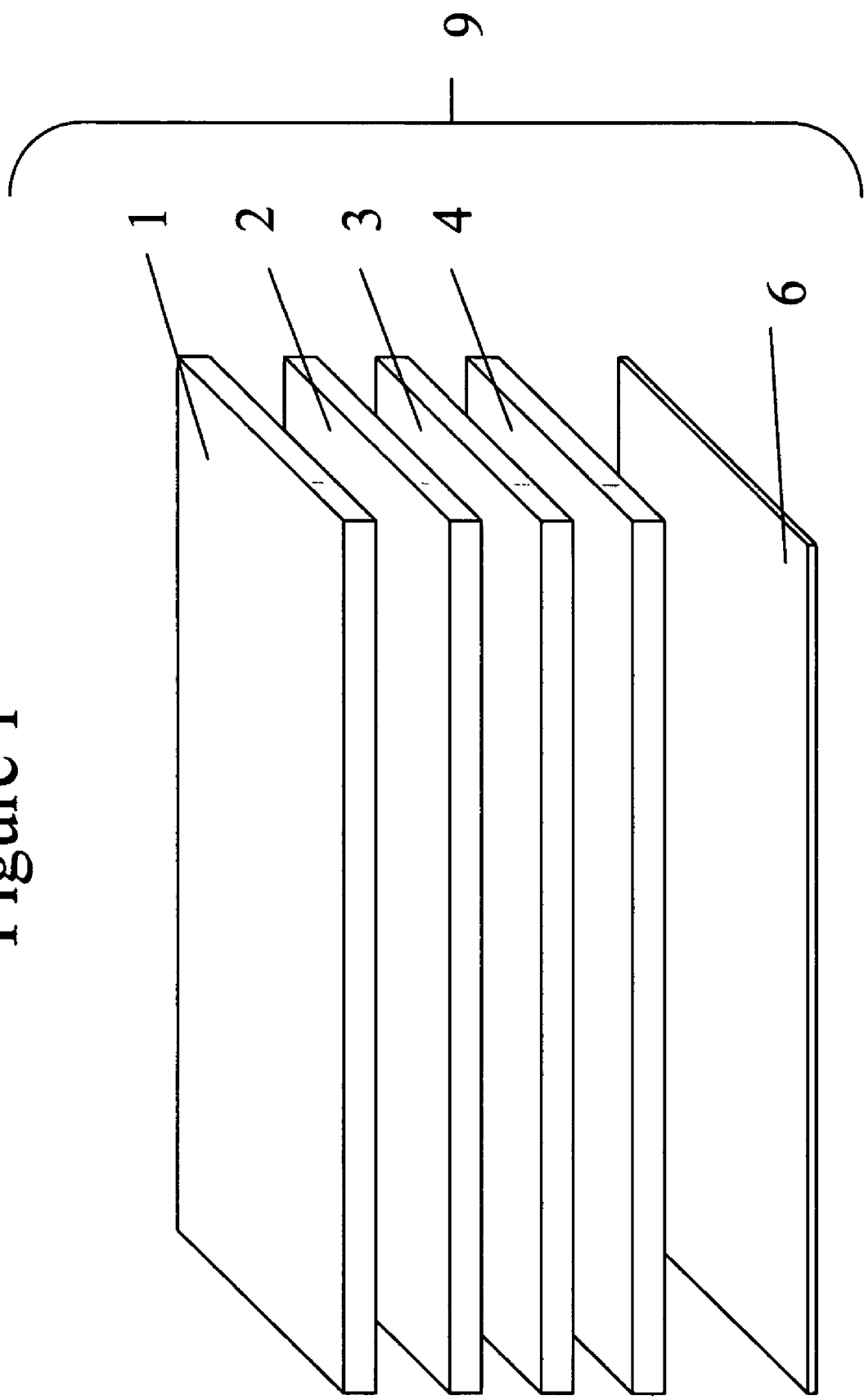

The Michael addition oligomers comprise the reaction product of a β-dicarbonyl compound (Michael donor) such as β-ketoester, β-diketone, β-ketoamide, β-ketoanilide or mixture thereof and a multiacrylate compound having at least one isocyanate reactive group and/or a mixture of an acrylate compound having at least one isocyanate reactive group and at least one multiacrylate compound (Michael acceptors). The Michael addition oligomers are prepared by known methods such as those disclosed in U.S. Pat. Nos. 5,945,489 and 6,025,410. The Michael addition oligomer used in the current invention has on average one isocyanate reactive group and at least 1.5 free acrylate groups per mole.

Examples of the β-dicarbonyl compound include β-dicarbonyl compounds having functionality of 2 such as, ethyl acetoacetate, methyl acetoacetate, 2-ethylhexyl acetoacetate, lauryl acetoacetate, t-butyl acetoacetate, acetoacetanilide, N-alkyl acetoacetanilide, acetoacetamide, 2-acetoacetoxylethyl acrylate, 2-acetoacetoxylethyl methacrylate, allyl acetoacetate, benzyl acetoacetate, 2,4-pentanedione, isobutyl acetoacetate, and 2-methoxyethyl acetoacetate.

Suitable β-dicarbonyl donor compounds having functionality of 4 include 1,4-butanediol diacetoacetate, 1,6-hexanediol diacetoacetate, neopentyl glycol diacetoacetate, cyclohexane dimethanol diacetoacetate, and ethoxylated bisphenol A diacetoacetate.

Suitable β-dicarbonyl donor compounds having functionality of 6 include, trimethylol propane triacetoacetate, glycerin triacetoacetate, and polycaprolactone triacetoacetates.

Suitable multiacrylate compounds having at least one isocyanate reactive group includes those acrylates having more than one acrylate group per molecule and at least one isocyanate reactive group per molecule. Examples of isocyanate reactive groups includes epoxy, hydroxyl, amine and thiol groups. A suitable multiacrylate compound having at least one isocyanate reactive group includes pentaerythritol triacrylate.

Suitable acrylates having at least one isocyanate reactive group are monoacrylates having at least one isocyanate reactive group. Examples include 2-hydroxyethylacrylate, 2-hydroxypropylacrylate, 4-hydroxybutylacrylate, 8-lactone extensions of hydroxyethyl, hydroxypropyl or hyroxybutylacrylate containing δ-caprolactone moieties; γ-butyrolactone extensions of hydroxyethyl, hydroxypropyl or hydroxybutylacrylate containing 1-4 γ-butyrolactone; polyalkoxylate adducts of hydroxyethyl, hydroxypropyl and hydroxybutylacrylates based on ethylene and propylene oxide and lactoyl lactate derivatives of hydroxyalkylesters of acrylic acid.

Multiacrylates are acrylates free of isocyanate reactive groups and having more than one acrylate group. Examples include diethyleneglycol diacrylate, polyethyleneglycol diacrylate, ethoxylated bisphenol A diacrylate, trimethylolpropane triacrylate (TMPTA), ethoxylated and propoxylated TMPTA, propoxylated glyceryl triacrylate and pentaerythritol tetraacrylate (PETA).

The Michael addition reaction is catalyzed by a strong base. An example of such a base is diazabicycloundecene (DBU), which is sufficiently strong and is readily soluble in the monomer mixtures. Other cyclic amidines, for example diazabicyclo-nonene (DBN) and guanidines are also suitable for catalyzing this reaction. Group I alkoxide bases such as potassium tert-butoxide, provided they have sufficient solubility in the reaction medium, are also typically adequate to promote the desired reaction. Quaternary hydroxides and alkoxides, such as tetrabutyl ammonium hydroxide or benzyltrimethyl ammonium methoxide, comprise another class of base catalysts that promote the Michael addition reaction. Finally, strong, organophilic alkoxide bases can be generated in situ from the reaction between a halide anion (e.g., quaternary halide) and an epoxide moiety. Such in situ catalysts are disclosed in pending application Ser. No. 10/255,541 assigned to Ashland Inc., the assignee of the present application. The entire contents of application Ser. No. 10/255,541 are specifically incorporated by reference in its entirety and for all purposes.

The isocyanate terminated butadienes used to form the liquid oligomeric compositions are the reaction product of a hydroxyl capped polybutadiene and an isocyanate such as toluene diisocyanate, diphenylmethane diisocyanate and the like. Examples of commercially available polybutadienes include the materials from Sartomer under the trademark Krasol. The preferred polybutadiene is an essentially difunctional molecule with little or no functional groups attached along the backbone of the polybutadiene. The Michael addition oligomers are reacted with an isocyanate terminated butadiene preferrably in the presence of a catalyst to promote the reaction between the isocyanate reactive group and the terminal isocyante groups of the butadiene molecule. The catalyst(s) used are those known in the art to promote the formation of the urethanes. Examples of suitable catalysts include tertiary amines and tin (II) and tin (IV) salts of carboxylic acids. Examples of tertiary amines includes N-ethyl morpholine, N,N,N',N'-tertamethylethylene diamine, 1,4-diazobicyclo-(2,2,2)-octane, 1,2-dimethyl imidazole and the like. Examples of tin (II) and tin (IV) salts of carboxylic acids include tin (II)-acetate, tin (II)-laurate, dibutyl tin dilaurate, dioctyl tin diacetate and the like.

In general the UV curable liquid oligomeric composition is prepared and then the fragrance/solvent blend is added. The resulting residue of the UV cured liquid oligomeric composition releases the fragrance/solvent blend in a controlled manner.

Photoinitiators can be used to cure the present UV curable, liquid oligomeric compositions but the photoinitiator is present in significantly reduced amounts when compared to known UV curable compositions. Typical levels for photoinitiators in conventional UV curable resin formulations can be 10 wt. %. Photoinitiators used in the present invention are present in amounts from 0 to 5 wt % based on the total weight of the liquid UV curable oligomeric composition. The range of photoinitiator used is dictated by any number of factors including opacity, thickness of the film, etc. and is typically from about 2.0 to about 4.0 wt %.

Examples of suitable photoinitiators include those known in the art such as benzoin, benzoin methyl ether, 2-benzyl-2-dimethylamino-1-(4-morpholinophenyl)-1-butanone, 1-hydroxycyclohexyl phenyl ketone, benzophenone, 4-phenyl benzophenone, acetophenone, diphenyl(2,4,6-trimethylbenzoyl)phosphine oxide (TPO) and the like.

The structure of the UV curable, liquid oligomeric composition incorporating a polybutadiene, provides a composition accepting of fragrance based material while overcoming the deficiencies of typical UV curable materials. The presence of the polybutadiene enhances the flexibility of the oligomeric composition allowing for thick films of fragrance containing compositions. In addition the UV curable, liquid, oligomeric compositions do not require the presence of monomers such as acrylic and/or methacrylic monomers to cure.

In addition, other materials and additives may be incorporated into the UV curable, liquid oligomeric composition. These might include fillers, catalysts, dyes, UV stabilizers and tackifiers. Examples of these materials would be tackifiers based upon rosin ester or terpenes. Examples of dyes would be those that are commercially available, soluble in organic solvents and compatible with the fragrance/resin mixtures.

Said UV curable, liquid oligomeric composition produces unique gel systems as residue when radiation cured in combination with fragrances. Said fragrance gels have been shown to hold fragrance molecules and their excipient or carrier solvents at high levels and to release said fragrances in a controlled, sustained fashion.

On cure, the fragrance, carrier solvent, matrix gel system contains swelled polybutadiene domains carrying the incorporated fragrance and its solvent. In the subject system, the most effective solvents are those which have a high polarity as well as hydrophobiscity. An example of this would be the hexane glycols. These systems readily compatibilize with the polybutadiene segments through their aliphatic constituents, while their hydroxyl constituents bond with the polar fragrance molecules. Diffusion of the solvent to the gel surface also results in a migration of the fragrance to the surface since it is dragged along through the polar interactions. Evaporation of solvent at the gel surface decreases surface polarity and increases the ease of fragrance molecule volatilization.

Acrylated urethane capped versions of the polybutadiene oligomer described in this invention are capable of forming fragrance containing films, but show substantial shrinkage during the fragrance release cycle in comparison with fragrance containing films prepared using the UV curable, oligomer systems taught in this invention. The present invention overcomes the problem of substantial shrinkage and subsequent discoloration and cracking.

An example of the propensity of the residue of the fragrance doped UV cured, liquid oligomeric composition to controllably release fragrance is demonstrated in Tables 1, 2 and 3.

TABLE 1

Loss of mass (g) over time in a dynamic environment as determined by gravimetric analysis.

|  | Sample 1 | Sample 2 | Sample 3 | Sample 4 |
| --- | --- | --- | --- | --- |
| Original Mass (g) | 19.147 | 17.656 | 25.16 | 26.39 |
| Last Day Measured | Day 45 | Day 45 | Day 45 | Day 45 |
| Final Mass (g) | 18.901 | 16.992 | 24.475 | 25.297 |
| Original Fragrance Mass (g) | 1.092 | 1.1848 | 2.3667 | 2.3836 |
| Total Loss of Fragrance Mass (g) | 0.2454 | 0.6645 | 0.685 | 0.4835 |
| Mass % Loss of Fragrance | 22.47 | 56.09 | 28.94 | 20.28 |
| Top Layer Oligomer:Fragrance Conc., Mass % | 33 | 60 | 33 | 15 |
| Bottom Layer Oligomer:Fragrance Conc., Mass % | N/A | N/A | 60 | 60 |
| Number of fragrance containing oligomer layers | 1 | 1 | 2 | 2 |
| Fragrance | BELMAY Lemon-lime | BELMAY Lemon-lime | BELMAY Lemon-lime | BELMAY Lemon-lime |

TABLE 2

Fragrance Sustenance Over Time - Static Air Flow

|  | Fragrance apparent | Noticeable Change in Fragrance Strength from Previous Week |
| --- | --- | --- |
| Week 1 | Yes | N/A |
| Week 2 | Yes | N/A |
| Week 3 | Yes | N/A |
| Week 4 | Yes | N/A |
| Week 5 | Yes | N/A |
| Week 6 | Yes | Yes |
| Week 7 | Yes | Yes |

TABLE 3

Fragrance Sustenance Over Time - Continuous Air Flow

|  | Fragrance apparent | Noticeable Change in Fragrance Strength from Previous Week |
| --- | --- | --- |
| Week 1 | Yes | None (Strong) |
| Week 2 | Yes | None (Strong) |
| Week 3 | Yes | Yes (Weaker) |
| Week 4 | Yes | Yes (Weaker) |
| Week 5 | Yes | Yes (Weaker) |
| Week 6 | Yes | Yes (Weaker) |
| Week 7 | N/A | N/A |

The samples were prepared using approximately 3.5 g of a fragrance/solvent blend containing the UV curable, liquid oligomeric composition and were coated on to 3"×3" polycarbonate squares. These coatings were cured using an H bulb source with a line speed between 30-40 fpm.

The evaluation of fragrance duration over time was determined by the measurement of the loss of mass of a fragrance doped, UV cured, oligomeric composition of the present invention cast in sheet form, at various time intervals as measured by simple gravimetric analysis. The rate of release was also calculated from the gravimetric data taken at the various time intervals. Fragrance sustenance was evaluated subjectively by determining if the fragrance was apparent and if so, has the fragrance intensity changed from the last measurement.

The present invention can take the form of many embodiments due to its versatile nature. It may be utilized as a single layer or as part of a multi-layer device. The UV curable, liquid oligomeric composition of the present invention can act as both a reservoir impregnated with fragrance and as a regulating layer or coating that would control the release of fragrance from an underlying reservoir. It can function as a three dimensional, aesthetically pleasing sculptured air freshener or a two dimensional, flat air freshener that is inconspicuous. The multi-layered device can include an image bearing layer that is viewable through the device.

One embodiment of the present invention involves the placement of a thin single-layer or multi-layer device within the vehicle interior and affixed to a window. Such a device can be affixed using an adhesive or by creating an adhesive surface by inhibiting the cure of the UV curable, oligomeric composition layer. The adhesive surface would be protected by a peelable protective coating or sheet. An additional method of affixation would involve the adhesion of the UV curable, oligomeric composition layer to a laminate that has the capability of supporting the entire device by static cling against the vehicle window. Alternative embodiments would involve shaping the air freshener into either a two or three-dimensional shape that is aesthetically pleasing. Additionally, the device could be made to be mostly transparent and an image bearing layer could be included within the device to display a picture, logo, or other illustration.

A first example of adhesively affixed device is depicted in FIG. 1. In FIG. 1, the device 9 is shown as a stacked series of layers that contain a fragrance impregnated gel layer 1 that is bonded to a first adhesive layer 2. The fragrance impregnated gel layer is preferably the novel UV curable, oligomeric composition but may also be SYLVAGEL™, EVA (ethyl vinyl acetate), or a similar polymer or oligomer which can store and controllably release fragrant materials. The adhesive layer 2 is adhesively attached to an image bearing film layer 3 which may be viewed through a sufficiently transparent gel and adhesive. Underlying the image bearing film layer 3 is a second adhesive layer 4 which is protected by a peelable protective film 5 that allows the adhesive to bond to a surface when removed. An alternative embodiment is depicted in FIG. 3, where the air freshener device 29 utilizes a UV curable, oligomeric composition with adhesive properties.

Figure 2:
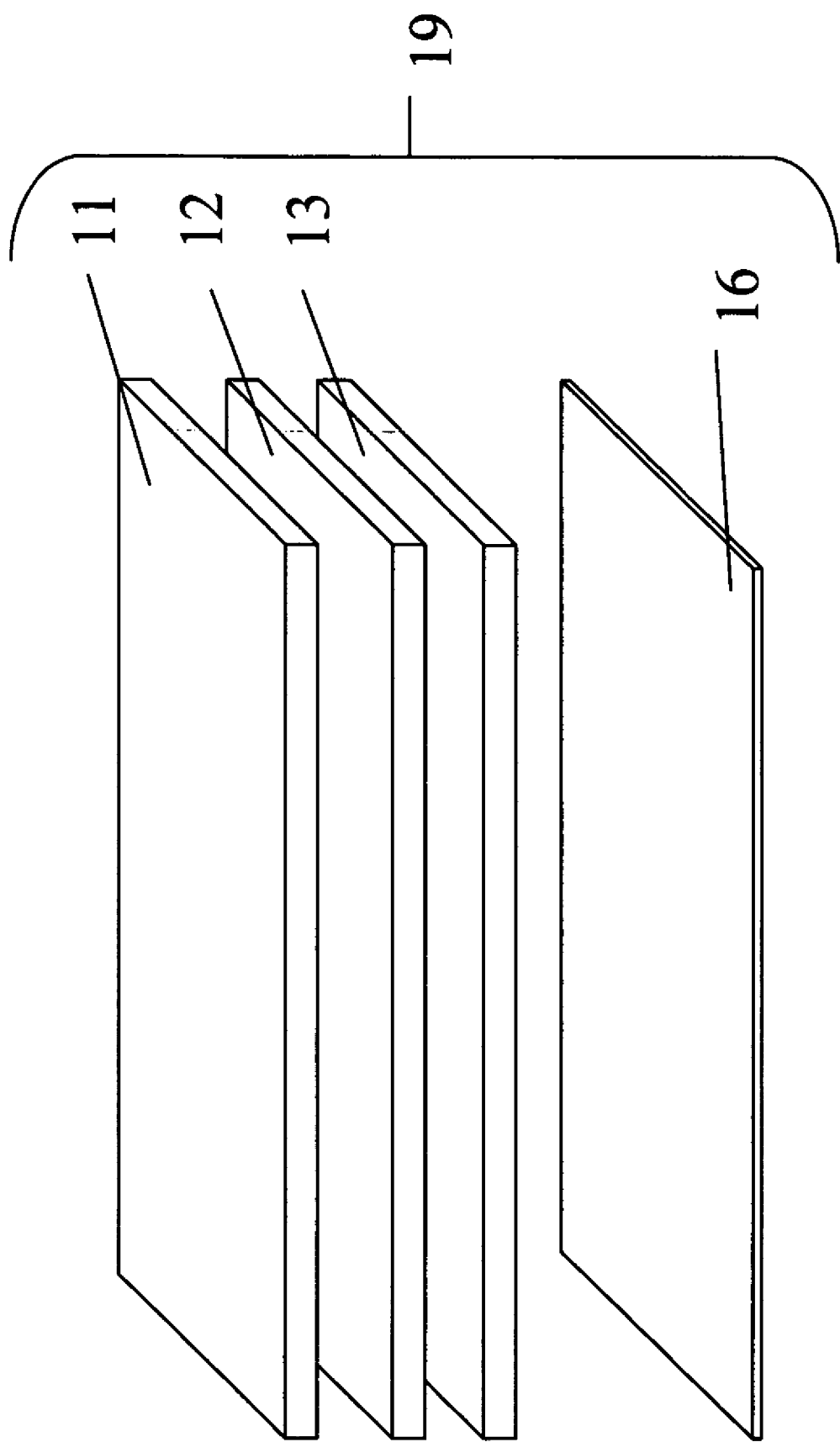

FIG. 2 depicts an air freshener device 19 which utilizes an adhesive UV curable, oligomeric composition or similar system, a fragrance reservoir layer 11 bonded to an image bearing layer 12 thereby eliminating the need for an adhesive layer to bond the fragrance reservoir 11 to an image bearing layer 12. The image bearing layer caps an adhesive layer 13 which will bond to a surface when the peelable protective film 16 is removed.

Figure 3:
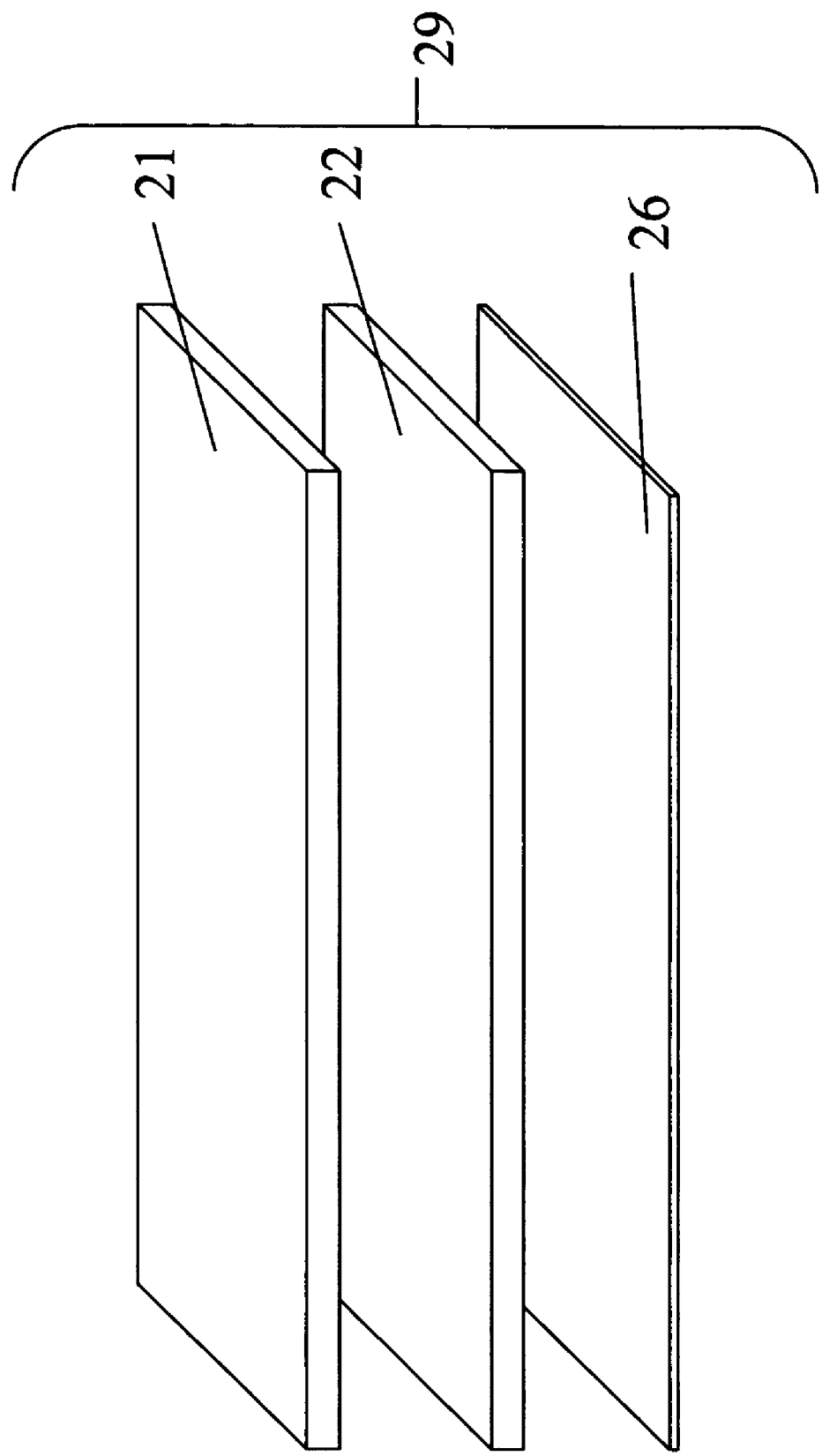

FIG. 3 depicts an air freshener device 29 utilizing an image bearing static cling layer 22 beneath the transparent cure inhibited oligomeric system functioning as a fragrance reservoir layer 21. The static cling layer adheres to a glass surface such as a car window.

Figure 4:
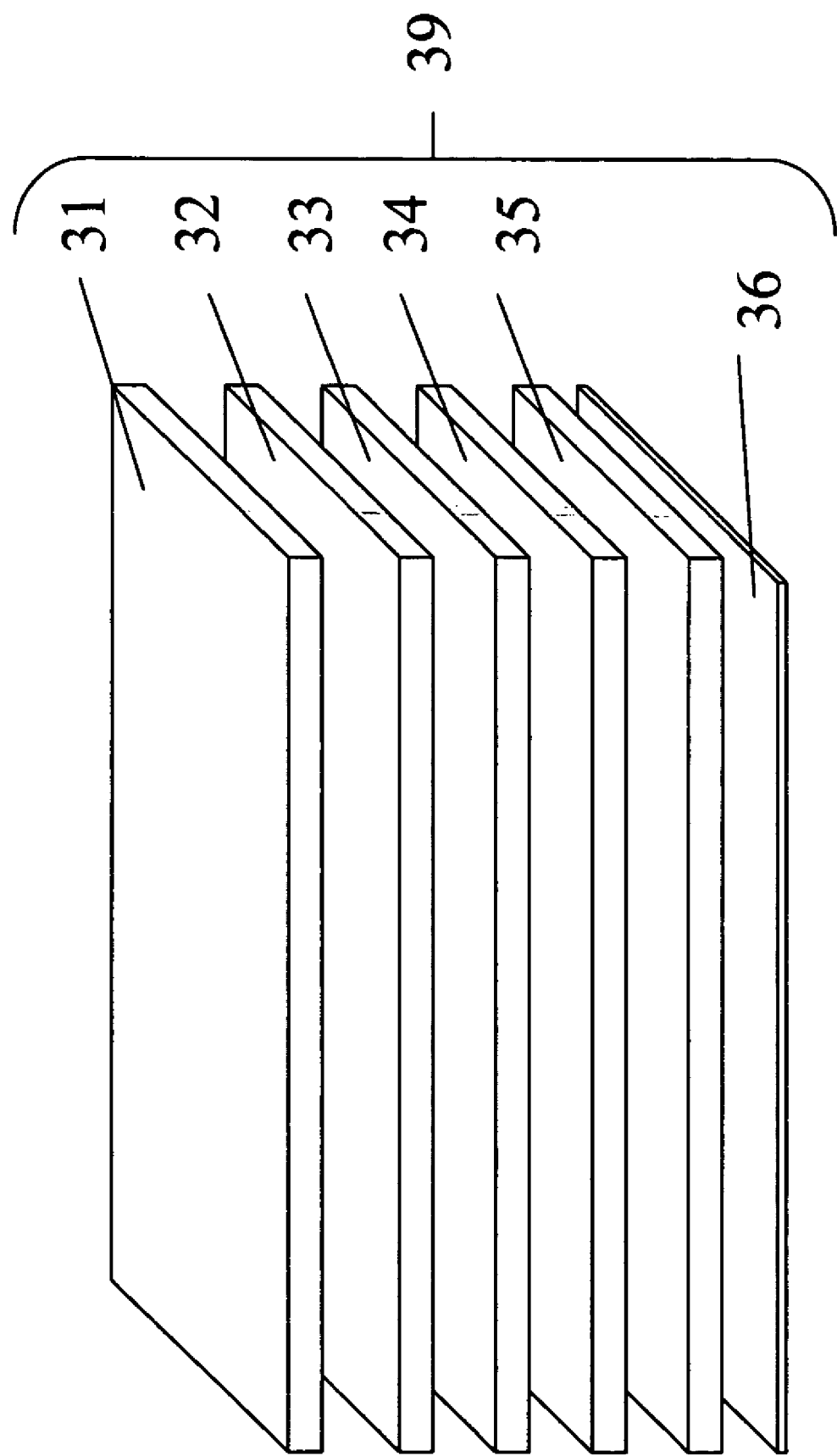

An additional embodiment is depicted in FIG. 4, where air freshener device 39 is comprised of a fragrance impregnated gel layer or fragrance reservoir 32 which is capped with a regulating layer 31 which functions to regulate or control the release of fragrant material from the fragrance reservoir 32 to the environment. The regulating layer 31 may be either a semi-permeable gel or resin layer or preferably a second radiation cured gel, such as the aforementioned UV curable, liquid oligomeric composition. The second radiation cured gel can be doped with fragrance to improve the transfer of the excipient solvent and fragrance from the first radiation cured gel, or fragrance reservoir 32, to the second radiation cured gel, resin, UV curable oligomeric composition of the present invention, or regulating layer 31. The device may optionally contain an image bearing film 34 which is optionally adhered to the fragrance reservoir 32 by a first adhesive layer 13 and to a surface by a second adhesive layer 35 which is protected by a peelable protective coating 36. When the fragrance reservoir 32 is the UV curable, liquid oligomeric composition, the first adhesive layer 33 may be eliminated from the device 39. A variation on the device depicted in FIG. 2 would involve utilization of the UV curable, liquid oligomeric composition, having been engineered to have an adhesive or tacky surface through the surface application of cure inhibitors, acting as the regulating layer 31 and a fragrance reservoir 32 comprised of commonly utilized polymeric such as EVA (ethyl vinyl acetate) and sylvagel to name a few non-limiting examples.

FIG. 5 depicts a hanging type system 49 which is comprised of a regulating layer 41 as previously described, a fragrance reservoir 42, and an image bearing sheet 43 preferably made of rigid plastic. The exposed surface of the regulating layer 41 is protected by a peelable protective film 46. An alternative embodiment to FIG. 5 is depicted in FIG. 6 with the image bearing sheet 53 encasing the fragrance reservoir and/or regulating layer leaving only the exposed surface 51 to top layer of the device 59, preferably the previously described regulating layer, in contact with the environment. This prolongs the life of the device and provides additional control over the release of fragrant materials into the environment. This embodiment of this invention anticipates partially encasing the fragrance reservoir and regulating layer in frames like structures and holders so as to limit the amount of exposed surface area in an effort to prolong the lifespan of the air freshening device.

FIG. 7 depicts a cutaway view of an air freshener device 69 comprised of a paper blotter or other fragrance reservoir 62 encapsulated by a regulating layer 61 as previously described. The system could take any shape the manufacturer desires, even three-dimensional creations such as symbols, animals, mascots, or other artistic and aesthetically pleasing forms. The devices could be hung, adhered to surfaces using adhesives or by selectively curing one side of the UV curable, oligomeric composition acting as the regulating layer 61, placed under a car seat, placed within the ventilation system, or located in any other convenient location.

This embodiment of the invention anticipates utilizing capillaries, veins, or similar encapsulated areas of fragrant material containing UV curable, oligomeric composition gels to allow the creation of unique and attractive air freshening devices. Continuous contact between a larger reservoir and remote regions of such a device would allow replenishment of fragrant material at these remote regions thus increasing the useful life of the air freshener. One such embodiment would take the form of a whiskerball, wherein the center would be a larger reservoir and the extremities would permit rapid diffusion of the fragrance into the surrounding environment.

Having thus described the invention, the following examples are provided for illustration purposes only.

Example 1

Preparation of Hydroxyl-Functional Michael Adduct

Into a 1000 ml. cylindrical glass reactor were placed 41.94 g. (0.3223 mol.) ethyl acetoacetate, 41.17 g. (0.3545 mol.) 2-hydroxyethyl acrylate, 105.05 g. (0.3545 mol.) trimethylolpropane triacrylate, 1.98 g. (0.00614 mol.) tetrabutylammonium bromide catalyst, and 7.92 g. (0.0557 mol.) glycidyl methacrylate co-catalyst. The flask was fitted with a heating mantle and capped with a reactor cover fitted with a mechanical stirrer, thermometer, and reflux condenser. The reaction mixture was stirred and heated to 95° C. in one hour. The mixture was held at 95° C. and monitored by refractive index and viscosity (Brookfield CAP2000L cone and plate viscometer with Cone #06). After two hours, the refractive index reached 1.4816 (25° C.) and viscosity reached 53.5 poise at 25° C. (500 rpm, 30 sec.). The reaction mixture was then cooled to 50° C. and the catalyst was quenched with 1.94 g. (0.00922 mol.) Ebecryl® 168 (UCB Chemicals). The finished Michael adduct was obtained after stirring at 50° C. an additional 15 minutes.

Example 2

Reaction of Michael Adduct with Isocyanate-Capped Polybutadiene

The reactor containing the adduct of Example 1 (1846.6 g) was flushed and blanketed with dry air. To the reactor was added Krasol LBD 2000 (4616.4 g) (toluene diisocyanate polybutadiene prepolymer from Sartomer Company), dibutyltin dilaurate (3.9 g), hydroquinone (0.162 g) and 1,4 naphthoquinone (0.388 g). The mixture was heated with stirring to 80° C. over a one hour period. At the end the hour the pressure in the reactor was reduced 28 mm Hg while the temperature was held constant at 80° C. for 90 minutes. The reactor was brought back to atmospheric conditions. Dipropylene glycol (124.4 g) was added to the mixture. The contents of the reactor were allowed to stir for 30 minutes. A fragrance/solvent blend (3185.4 g) was then added to the reactor along with Irgacure 184 (193.6 g) and Genocure TPO (29.2).

Sample Preparation

Approximately 3.5 g of a 33% fragrance/solvent blend containing UV curable, liquid oligomeric composition (Example 2) were coated on to 3"×3" polycarbonate squares. These coatings were cured using an H bulb source with a line speed between 30-40 fpm. Two samples of each fragrance/solvent blend were prepared. One sample of the residue of the UV cured liquid oligomeric composition and fragrance/solvent blend was placed in a cubicle office. The other sample was placed in a exhaust hood. These will be referred to in the tables as static (S) and dynamic (D) environments. The following table shows a summary of the total weight loss of the sample, the theoretical amount of fragrance in the sample and the percent of "fragrance" remaining. The table below shows typical weight loss data and detectable fragrance data for samples produced with this novel UV curable, liquid oligomeric composition.

TABLE 4

Fragrance Retention in Static and Dynamic Environments

| Sample | Days | Initial Fragrance Mass (g) | Total Mass Lost (g) | Theoretical Percentage of Initial Fragrance Remaining (mass %) |
| --- | --- | --- | --- | --- |
| 1 layer-33% Country Berries (S) | 44 | 1.0036 | 0.5923 | 41.0 |
| 1 layer-33% Country Berries (D) | 44 | 1.0224 | 0.5788 | 43.4 |
| 1 layer-33% Rain Forest (S) | 45 | 0.974 | 0.4491 | 53.9 |
| 1 layer-33% Rain Forest (D) | 45 | 0.9685 | 0.4176 | 56.9 |

TABLE 5

Fragrance Detectable by Smell

| Sample | 29 days | 45 days |
| --- | --- | --- |
| 1 layer-33% Country Berries (S) | Yes | No |
| 1 layer-33% Country Berries (D) | Yes | No |
| 1 layer-33% Rain Forest (S) | Yes | Yes |
| 1 layer-33% Rain Forest (D) | Yes | No |

The key here is that the samples have detectable fragrance for nearly 30 days and in one case 45 days. This is a significant improvement over current paper products which may last 10-14 days.

Further samples were tested for 30 days only.

Sample Preparations

A "picture frame" is created out of 4 tongue depressors and mounted to a polyester sheet. This frame creates the boundaries in which a 33% fragrance containing UV curable, liquid oligomeric composition sample is poured. The typical sample dimensions are approximately 2"×2"×1.5 mm. The UV curable, liquid oligomeric composition sample is cured similar to the examples above. After curing, the frame is removed to yield a UV cured, fragrance containing liquid oligomeric composition sample. The weight loss data for some representative samples is listed below. The testing was conducted for a period of only 30 days. These samples are compared to a paper blotter sample which has dimensions of 3½"×2¾"×2.4 mm. The paper blotter is dosed with 2.0 g of fragrance. The samples are place in a Rubbermaid container (12 qt.) for a period of 15 min. to help determine the level of fragrance released.

TABLE 6

Fragrance Retention in Static and Dynamic Environments

| Sample | Days | Initial Fragrance Mass (g) | Total Mass Lost (g) | Theoretical Percentage of Initial Fragrance Remaining (mass %) |
| --- | --- | --- | --- | --- |
| 1 layer-33% Country Berries | 30 | 1.444 | 0.9189 | 36.4 |
| 1 layer-33% Vanilla Indulgence | 30 | 1.982 | 1.211 | 38.9 |
| 1 layer-33% Sparkling Citrus | 30 | 1.81 | 1.026 | 43.3 |
| 1 layer-33% Rain Garden | 30 | 1.905 | 1.019 | 46.5 |
| 1 layer-33% Vanilla Breeze | 30 | 1.705 | 1.227 | 28.1 |

TABLE 7

Fragrance Detectable by Smell by Reservoir at 35 Days

| Sample | UV Curable, Liquid Oligomeric Composition | Paper Blotter |
| --- | --- | --- |
| 33% Country Berries | Moderate | Moderate |
| 33% Vanilla Indulgence | Moderate | Slight |
| 33% Sparkling Citrus | Slight to Moderate | Very Slight |
| 33% Rain Garden | Slight | Slight |
| 33% Vanilla Breeze | Very Slight | None |

What is claimed is:

1. An air freshening device comprising:
   a cured residue of a UV curable, liquid oligomeric composition comprising β-dicarbonyl donor compounds with mixtures of hydroxyl-functional acrylates and multi-functional acrylate receptor compounds and isocyanate capped polybutadiene impregnated with a fragrant material and a solvent wherein said oligomeric composition is cure inhibited;

at least one tackifier;

an adhesive layer; and a reservoir layer impregnated with a fragrant material and a solvent.

2. The device of claim 1, wherein the oligomers of said UV curable, liquid oligomeric composition possess acrylate unsaturation and polybutadiene segments.

3. The device of claim 1, wherein said tackifiers are selected from the group consisting of rosin esters and terpenes.

4. The device of claim 1, wherein said UV curable, liquid oligomeric composition is partially cure inhibited.

5. The device of claim 1, wherein said UV cured, liquid oligomeric composition is transparent.

6. The device of claim 1, wherein at least one layer bears an image for display.

7. The device of claim 1, wherein said UV curable, liquid oligomeric composition encases said reservoir layer.

8. The device of claim 1, wherein said reservoir layer is constructed from the group consisting of ethyl vinyl acetate; UV curable, liquid oligomeric composition; paper; silicone based polymers; and similarly available substances capable of retaining and releasing a fragrant material.

9. The device of claim 1, wherein said reservoir layer is transparent.

10. The device of claim 1, wherein said UV curable, liquid oligomeric composition is of higher cross-link density than said reservoir layer.

11. The device of 1, wherein said solvent is a polar organic solvent.

12. The device of claim 1, wherein said UV curable, liquid oligomeric composition is imprintable with ink.

13. The device of claim 12, wherein said UV curable, liquid oligomeric composition is imprintable with ink from a printer selected from the group consisting of laser printers, ink jet printers, bubble jet printers, and similar commercially available printers.

* * * * *

UNITED STATES PATENT AND TRADEMARK OFFICE
CERTIFICATE OF CORRECTION

| | | |
|---|---|---|
| PATENT NO. | : 7,651,763 B2 | Page 1 of 1 |
| APPLICATION NO. | : 10/967448 | |
| DATED | : January 26, 2010 | |
| INVENTOR(S) | : David Allen Hutchings et al. | |

It is certified that error appears in the above-identified patent and that said Letters Patent is hereby corrected as shown below:

Column 2, cover page, Abstract item 57, lines 10-11 "oligomer composition acting a fragrance" change to -- oligomer composition acting as a fragrance--.
Column 1, line 34 "device not a multi-laminate" change to -- device is not a multi-laminate --.
Column 2, line 23 "the all of the devices occupy" change to -- all of the devices occupy --.
Column 2, line 67 "higher viscosity and cross-link density of ... produces a device" change to -- higher viscosity and cross-line density of ... produce a device --.
Column 4, lines 11-13 "This additional layer acts to further control diffusion and thus regulate the release of the fragrance to achieve a release which is both prolonged and consistent over time." change to -- delete this sentence --.
Column 4, lines 42-43 "device is dependant upon" change to -- device is dependent upon --.
Column 4, line 58 "FIG. 1-5 are" change to -- FIGS. 1-5 are --.
Column 5, lines 29-30 "compounds having ... includes those" change to -- compounds having ... include those --.
Column 5, lines 31-32 "Examples of ... includes" change to -- Examples of ... include --.
Column 6, line 26 "tertamethyethylene" change to -- tetramethylethylene --.
Column 10, line 10 "frames like structures" change to -- frame-like structures --.
Column 11, line 5 "At the end the hour the" change to -- At the end of the hour the --.
Column 14, line 11, Claim 11 "The device of 1, wherein" change to --The device of claim 1, wherein --.

Signed and Sealed this
Twenty-first Day of February, 2012

David J. Kappos
*Director of the United States Patent and Trademark Office*